United States Patent
Kaser et al.

(10) Patent No.: US 6,168,933 B1
(45) Date of Patent: Jan. 2, 2001

(54) PHOSPHOLIPID TRANSFER PROTEIN

(75) Inventors: Matthew R. Kaser, Castro Valley; Jennifer L. Hillman, Mountain View; Mariah R. Baughn, San Leandro, all of CA (US)

(73) Assignee: Incyte Pharmaceuticals, Inc., Palo Alto, CA (US)

( * ) Notice: Under 35 U.S.C. 154(b), the term of this patent shall be extended for 0 days.

(21) Appl. No.: 09/328,869

(22) Filed: Jun. 8, 1999

(51) Int. Cl.$^7$ .......................... C12P 19/34; C12P 21/06; C12Q 1/68; G01N 33/00; C07H 21/02

(52) U.S. Cl. .......................... 435/91.1; 435/6; 435/91.2; 435/69.1; 536/23.1; 436/94

(58) Field of Search .............................. 435/6, 91.1, 91.2, 435/183; 436/94; 536/23.1, 24.3, 24.33, 25.3

(56) References Cited

PUBLICATIONS

Lin, comparative gene cloning: identification of novel human genes with Caenorhabditis elegans proteome as template. Submitted (May 17, 1999, accession No. AF 151810) to the EMBL/GenBank/DDBJ data base.*

Geijtenbeek, T.B.H. et al., "cDNA cloning and tissue–specific expression of the phosphatidylcholine transfer protein gene", *Biochem Journal*, 316: 49–55 (1996).

Chen, S. et al., "Phosphatidylcholine Transfer Protein From Porcine Liver", *Biochemistry International*, 23(2): 377–382 (1991).

Feng, L. and D.E. Cohen, "Baculovirus–mediated expression of recombinant rat phosphatidylcholine transfer protein", *Journal of Lipid Research*, 39:1862–1869 (1998).

LaMorte, W.W. et al, "Determinants of the Selection of Phosphatidylcholine Molecular Species for Secretion into Bile in the Rat", *Hepatology*, 28(3): 631–637 (1998).

Geijtenbeek, T.B.H. et al., "Phosphatidylcholine transfer protein from bovine liver contains highly unsaturated phosphatidylcholine species", *FEBS Letters*, 391:333–335 (1996).

Nicholas, T.E., "Pulmonary Surfactant: no mere paint on the alveolar wall", *Respirology*, 1: 247–257 (1996).

Griese, M. et al., "Pulmonary surfactant in cystic fibrosis", *European Respiratory Journal*, 10: 1983–1988 (1997).

Venkataramani, A. et al., "Abnormal Duodenal Bile Composition in Patients With Acalculous Chronic Cholecystitis", *The American Journal of Gastroenterology*, 93(3): 434–441 (1998).

Igal, R.A. and R.A. Coleman, "Neutral lipid storage disease: a genetic disorder with abnormalities in the regulation of phospholipid metabolism", *Journal of Lipid Research*, 39: 31–43 (1998).

Alb, J.G. et al., "Phospholipid metabolism and membrane dynamics", *Current Opinion in Cell Biology*, 8: 534–541 (1996).

Cockcroft, S., "Phosphatidylinositol transfer proteins: a requirement in signal transduction and vesicle traffic", *BioEssays*, 20: 423–432 (1998).

Bolton, A.E. and W.M. Hunter, "The Labelling of Proteins to High Specific Radioactivities by Conjugation to a $^{125}$I–Containing Acylating Agent", *Biochem. Journal*, 133: 529–539 (1973).

* cited by examiner

*Primary Examiner*—Bradley L. Sisson
*Assistant Examiner*—Frank Lu
(74) *Attorney, Agent, or Firm*—Incyte Genomics, Inc.; Lynn E. Murry

(57) ABSTRACT

The invention provides a mammalian nucleic acid molecule and fragments thereof. It also provides for the use of the nucleic acid molecule for the characterization, diagnosis, evaluation, treatment, or prevention of conditions, diseases and disorders associated with gene expression and for the production of a model system. The invention additionally provides expression vectors and host cells for the production of the protein encoded by the mammalian nucleic acid molecule.

13 Claims, 6 Drawing Sheets

```
                                    11          20          29          38          47          56
5' ATCGT TCT GTG GTC CTT TCT TTT ATG ATT CAC AAG GAA TGA CCC TCT TCA TCG CCT 65          74          83          92         101         110
    CTC CTA ATT CAG TCC TCA CAA CAG TCC TTT TAC AAA TGG GAC AAC AGG TTA GAG 119         128         137         146         155         164
    GAA GTC AGG CAG ATT TCC AGC ATC ATA GAG AGT AAA GGA CCA GGG AAG GAT CAG 173         182         191         200         209         218
    GAT TCA AGG ACT GCA CCC AGG CTC TGC TTC CAG CTT GCT GTG TGA CTT TGG GTA 227         236         245         254         263         272
    ATT TTG TTC CCT TAG GGA ACT GAG CTT TCT CAT TTG TAA ATG CAA ACA GGC TGT 281         290         299         308         317         326
    TGG GAG GAT CAA ATG AGA TCC AGG GGT GAA AAC AGC TTA GTT TAC TTT CAG GAA 335         344         353         362         371         380
    TTT ACC CAC GCG GTA TAT AAA GGC AAA ATA TTA TAG TCA GGT GAT TGT AGA
```

FIGURE 1A

```
       389       398       407       416       425       434
       TTG AGG AAC CCA TTT CCT CAT CCT GCA AAT TGC AAA CCT GAG GGC CCA AAG AGG 443       452       461       470       479       488
       GAC AGG GGC TTG CCC CAG GTC TCA GCA GGC TGT GAG CAA GAG CTA AAG CCT AAT 497       506       515       524       533       542
       CCT CCT GCC TTT GGG CCT GGA GCC CTT CCT TGT ACC CCA GGG GTC AGT GTC TTT 551       560       569       578       587       596
       GTT GGA TAC AGG CTT AGA TTG ACT GAC TGT ACC CTG AGA ACC TAG GGG AGT CCC 605       614       623       632       641       650
       TGT TCC CAA TTC TTC TCC TAC CCC CAC CTT GGC CTG ATG GAG GAA GAC CCT GCT 659       668       677       686       695       704
       GTG TTG AGA TGA GCA CCA GAG CCA AGA AGC TGA GGA GGA TCT GGA GAA TTC TGG 713       722       731       740       749       758
       AGG AAG AGA GTG TTG CTG GAG CTG TAC AGA CCC TGC TTC TCA GGT CCC AGG
```

FIGURE 1B

```
                                                                    812
                                                      803          AGG
                                        794          CCT   CCG   CGG
                             785       TTG   TCG   GAG
                  776       GCG   TCG   ACG
       767       TCT   GCA   GCC
AAG   GTG   GCA
      GCG
                                                                     866
                                                        857          ATG
                                          848          ACA   CTC   CCC   M
                              839        GCC   CTG   CCC
                  830        AGG   ACC
       821       ACT   AGG
ACC   CAG   AGC   CGG
      GAG
                                                                     920
                                                        911          CGT
                                          902          CTG   GGC    R
                              893        CCT   CGG   CCG
                  884        CAA   GGG   P     R     V     L     G
       875       ACA   GAG   Q
      GCC   TCT   E     P
GAG   CTG   A     S     T
      AAG   L
E     K
                                                                     974
                                                        965          TGT
                                          956          TCA   GAG     C
                              947        AGC   TTC   CGG    S    E
                  938        CAA   GAC   TTT   CGC          R
       929       GAT   GAC   TTG   ACC   Y     S     F
      GTC   CCC   Y     L     H
GAG   CAG   P     D     D
      AGT   V     Q
E     S
                                                                     1028
                                                      1019          TGG
                                        1010          TCT   GTC    W
                            1001       AAG   GCT   GGG   GTG    V
                  992       ACG   AGG   GCT   A     G
       983       GAT   CGG   W    N     R
      GGC   ATG   E     M     D
GAG   GAG   E     M
      GTG   A     V
GAG   GCT
E     A
                                                                     1082
                                                      1073          GAG
                                        1064          TGC   CGG   ATG   E
                              1055       AAG   ATC   AAG          R
                  1046        CTG   CAC              I     K     C
       1037       ATG   GAT   ACG   T     L     H     K
      GAG   GTG   T     Y     D     R
GTG   CAG   V     A     V
      CAG   V     P
GTG
V     Q
                                                                     1136
                                                      1127          TAC
                                        1118          CTA   CAC   GAG    Y
                              1109       GTC   CTA   ATT   GAC   TAC     E
                  1100        TAC                                     D    I
       1091       GCC   GAG          D     V     L     H     D     I
      GAT   GTG    T     L     Y
TGC   TGT   P     A
      CCA   D     V
GTG   C
      C
```

FIGURE 1C

```
     1145            1154            1163       1172            1181            1190
CGC AAG AAA TGG GAC AGC AAC GTC ATT GAG ACT TTT GAC ATC GCC CGC TTG ACA
 R   K   K   W   D   S   N   V   I   E   T   F   D   I   A   R   L   T 1199            1208            1217       1226            1235            1244
GTC AAC GCT GAC GTG GGC TAT TAC TCC TGG AGG TGT CCC AAG CCC CTG AAG AAC
 V   N   A   D   V   G   Y   Y   S   W   R   C   P   K   P   L   K   N 1253            1262            1271       1280            1289            1298
CGT GAT GTC ATC ACC CTC CGC TCC TGG CTC CCC ATG GGC GCT GAT TAC ATC ATT
 R   D   V   I   T   L   R   S   W   L   P   M   G   A   D   Y   I   I 1307            1316            1325       1334            1343            1352
ATG AAC TAC TCA GTC AAA CAT CCC AAA TAC CCA CCT CGG AAA GAC TTG GTC CGA
 M   N   Y   S   V   K   H   P   K   Y   P   P   R   K   D   L   V   R 1361            1370            1379       1388            1397            1406
GCT GTG TCC ATC CAG ACG GGC TAC CTC ATC CAG AGC ACA GGG CCC AAG AGC TGC
 A   V   S   I   Q   T   G   Y   L   I   Q   S   T   G   P   K   S   C 1415            1424            1433       1442            1451            1460
GTC ATC ACC TAC CTG GCC CAG GTG GAC CCC AAA GGC TCC TTA CCC AAG TGG GTG
 V   I   T   Y   L   A   Q   V   D   P   K   G   S   L   P   K   W   V 1469            1478            1487       1496            1505            1514
GTG AAT TCT TCT CAG TTC CTG GCT CCC AAG GCC ATG AAG AAG ATG TAC AAG
 V   N   S   S   Q   F   L   A   P   K   A   M   K   K   M   Y   K
```

FIGURE 1D

```
     1523            1532            1541            1550            1559            1568
GCG TGC CTC AAG TAC CCC GAG TGG AAA CAG AAG CAC CTG CCT CAC TTC AAG CCG
 A   C   L   K   Y   P   E   W   K   Q   K   H   L   P   H   F   K   P 1577            1586            1595            1604            1613            1622
TGG CTG CAC CCG GAG CAG AGC CCG TTG CCG AGC CTG GCG CTG TCG GAG CTG TCG
 W   L   H   P   E   Q   S   P   L   P   S   L   A   L   S   E   L   S 1631            1640            1649            1658            1667            1676
GTG CAG CAT GCG GAC TCA CTG GAG AAC ATC GAC GAG AGC GCG GTG GCC GAG AGC
 V   Q   H   A   D   S   L   E   N   I   D   E   S   A   V   A   E   S 1685            1694            1703            1712            1721            1730
AGA GAG CGG ATG GGC GCG GGC GGC GAG AGC GAC GAC GAC GAC ACC TCG
 R   E   R   M   G   A   G   G   E   S   D   D   D   D   T   S 1739            1748            1757            1766            1775            1784
CTC ACC TGA GCG CCG CAC CGC TTC AGG GAC GGA GAC AGG ACC CCC ACC CGG GCC CTG
 L   T 1793            1802            1811            1820            1829            1838
GGG CGG CGG CCG CCG CTG CAC TTT CTC CCC TCC CCC ACC CGG CAC CTG GTG GCA 1847            1856            1865
CCG GGC CAG GCC CAG GCG GGT GCT GCA  3'
```

FIGURE 1E

```
1772859   66  HKIKCRMECCDVPAETLYDVLHDIEYRKKWDSNVIETFDIARLTVNADVGYYSWRCPKPL  125
              +K+   +E C  PA L DV  D++YRK+WD  V E ++    +    V Y+  + P PL
GI 897786 14  YKVFGVLEGCS-PA-LLADVYMDLDYRKQWDQYVKELYE--KESDEQMVAYWEVKYPFPL  69

1772859  126  KNRDVITLRSWLPMGAD-----YIIMNYSVKHPKYPPRKDLVRAVSIQTGYLIQSTGPK-S  180
              NRD + R   + D       Y+++ S+  P++P + ++R  +    I+S G K S
GI 897786 70  SNRDYVYTRQRRDLDVDRRKIYVVLAQSISAPQFPEKSGVIRVKQYKQSLAIESDGKKGS  129

1772859  181  CVITYLAQVDPKGSLPKWVVNKSSQFLAPKAMKKMYKACLKY  222
              V  Y  +P G  +P W++N  +++    P  +K M KAC  Y
GI 897786 130 RVFMYYFD-NPGGQIPSWLINWAAKNGVPNFLKDMVKACQNY  170
```

FIGURE 2

PHOSPHOLIPID TRANSFER PROTEIN

FIELD OF THE INVENTION

This invention relates to nucleic acid molecules encoding a new mammalian protein and to the use of these molecules in the characterization, diagnosis, prevention, and treatment of conditions such as disorders associated with cell proliferation, lipid metabolism and transport.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general activity. Comparisons of human gene sequences with those from other organisms where structure and/or function are known allow researchers to draw analogies and to develop model systems for testing hypotheses. These model systems are of great importance in developing and testing diagnostic and therapeutic agents for human conditions, diseases, and disorders.

The phospholipid transfer protein family, important in phospholipid trafficking, includes phosphatidylinositol transfer protein (PI-TP, identical to yeast SEC14p), non-specific lipid transfer protein (nsL-TP, identical to sterol carrier protein 2), and phosphatidylcholine transfer protein (PC-TP). The sequence of PC-TP is unique and unrelated to other cytosolic lipid transfer proteins. It is encoded by a single gene and appears to be present in all eukaryotes (Geijtenbeek et al. (1996) Biochem. J. 316:49–55). Although amino acid compositions, molecular weights, and elution profiles of bovine and porcine PC-TP differ markedly, they retain similar transfer activity levels suggesting that amino acid composition of PC-TP can be altered without changing activity and specificity (Chen et al. (1991) Biochem. Int. 23:377–382).

PC-TP catalyzes PC intermembrane transfer (Feng and Cohen (1998) J. Lipid Res. 39:1862–1869), and certain PC molecular species are secreted preferentially into bile. Using multivariate analysis, LaMorte et al. (1998; Hepatology 28:631–637) examined the relationship between PC structure and the probability that individual PC species are secreted into the bile. They suggest that the likelihood of a PC being secreted into bile is closely related to its binding affinity for PC-TP.

Bovine liver PC-TP binds one molecule of PC noncovalently. Bound PC is not the predominant molecular species representative of bovine liver. Although PC species carrying a palmitoyl chain at the sn-1 position are abundant in bovine liver, they are rarely found bound as PC-TP. These findings led Geijtenbeek et al. (1996; FEBS Lett. 391:333–335) to suggest that PC-TP may have a role in the metabolism of highly unsaturated, stearoyl-containing PC molecular species.

PC is implicated in many different diseases relating to phospholipid metabolism, including neutral lipid storage disease (NLSD), lung diseases such as atelectasis, edema, and cystic fibrosis, and cholecystitis (Nicholas (1996) Respirology 1:247–257; Griese, et al. (1997) Eur. Respir. J. 10:1983–1988; and Venkataramani, et al. (1998) Am. J. Gastroenterol. 93:434–441). NLSD is a genetic disorder causing abnormalities in the regulation of phospholipid metabolism. Igal and Coleman (1998; J. Lipid Res. 39:31–43) suggest that an underlying regulatory defect in NLSD alters the rates of synthesis and degradation of the major cellular phospholipids including phosphatidylcholine and phosphatidyletha-nolamine.

Phosphatidylinositol-transfer proteins are important in vesicle-trafficking and signal-transduction (Cockcroft (1998) Bioessays 20:423–432; Alb, et al. (1996) Curr. Opin. Cell Biol. 8:534–541). Because PC-TP is a member of the family containing PI-TP, catalyzes PC intermembrane transfer (Feng and Cohen, supra), and is found in many organs (lung, kidney, testis, liver, etc.); PC is implicated in vesicle trafficking disorders and transport disorders. Therefore, the ability to control PC-TP provides the ability to intercede in disease processes.

The discovery of a nucleic acid molecule encoding a phospholipid transfer protein provides new compositions which are useful in the characterization, diagnosis, prevention, and treatment of disorders associated with cell proliferation, lipid metabolism and transport.

SUMMARY OF THE INVENTION

The invention is based on the discovery of a nucleic acid molecule encoding a mammalian protein, phospholipid transfer protein (PTP), which satisfies a need in the art by providing new compositions useful in the characterization, diagnosis, prevention, and treatment of conditions such as disorders associated with cell proliferation, lipid metabolism and transport.

The invention provides an isolated and purified mammalian nucleic acid molecule comprising SEQ ID NO:1 or a fragment thereof (SEQ ID NOs:3–11). The invention further provides fragments homologous to the mammalian nucleic acid molecules from rat identified as SEQ ID NOs:12–16 in the Sequence Listing. The invention also provides a substantially purified mammalian nucleic acid molecule encoding the amino acid sequence of SEQ ID NO:2 or a portion thereof.

The invention further provides an isolated and purified nucleic acid molecule or a fragment thereof which hybridizes under high stringency conditions to the nucleic acid sequence of SEQ ID NO:1. The invention also provides an isolated and purified nucleic acid molecule or a fragment thereof which is complementary to the nucleic acid sequence of SEQ ID NO:1. In one aspect, a single stranded complementary RNA or DNA molecule is used as a probe and hybridizes under high stringency conditions to the mammalian nucleic acid sequence or a fragment thereof.

The invention further provides a method for detecting a nucleic acid molecule in a sample, the method comprising the steps of hybridizing the probe to at least one nucleic acid sequence of the sample, thereby forming a hybridization complex; and detecting the hybridization complex, wherein the presence of the hybridization complex correlates with the presence of a nucleic acid sequence in the sample. In one aspect, the method further comprises amplifying the nucleic acid sequence prior to hybridization. The nucleic acid molecule or fragment thereof may comprise either an element or a target on a microarray. The invention also provides a method for using a nucleic acid sequence or a fragment thereof to screen a library of molecules to identify at least one molecule which specifically binds the nucleic acid sequence, the method comprising providing a library of molecules, combining the nucleic acid sequence with the library of molecules under conditions allowing specific binding, and detecting specific binding, thereby identifying a molecule which specifically binds the nucleic acid sequence. Such libraries include DNA and RNA molecules, peptides, PNAs, proteins, and the like which are potential regulators of replication, transcription, and translation. In an analogous method, the nucleic acid molecule or a fragment thereof is used to purify a ligand.

The invention also provides an expression vector containing at least a fragment of the nucleic acid molecule of SEQ ID NO:1. In another aspect, the expression vector is contained within a host cell. The invention further provides a method for producing a protein, the method comprising the steps of culturing the host cell under conditions for the expression of the protein and recovering the protein from the host cell culture. The invention also provides an isolated and purified protein comprising the amino acid sequence of SEQ ID NO:2 or a portion thereof. Additionally, the invention provides a pharmaceutical composition comprising a substantially purified protein having the amino acid sequence of SEQ ID NO:2 or a portion thereof in conjunction with a pharmaceutical carrier.

The invention further provides a method for using a portion of the protein to produce antibodies. The invention also provides a method for using a protein or a portion thereof to screen a library of molecules to identify at least one molecule which specifically binds the protein, the method comprising providing a library of molecules, combining the protein with the library of molecules under conditions allowing specific binding, and detecting specific binding, thereby identifying a molecule which specifically binds the protein. In one aspect, a molecule identified using the method modulates the activity of the protein. In an analogous method, the protein or a portion thereof is used to purify a ligand.

The invention further provides a method for inserting a marker gene into the genomic DNA of a mammal to disrupt the expression of the natural mammalian nucleic acid molecule. The invention also provides a method for using SEQ ID NO:1 to produce a mammalian model system, the method comprises constructing a vector containing SEQ ID NO:1; introducing the vector into a totipotent mammalian embryonic stem cell; selecting an embryonic stem cell with the vector integrated into genomic DNA; microinjecting the selected cell into a mammalian blastocyst, thereby forming a chimeric blastocyst; transferring the chimeric blastocyst into a pseudopregnant dam, wherein the dam gives birth to a chimeric mammal containing at least one additional copy of SEQ ID NO:1 in its germ line; and breeding the chimeric mammal to generate a homozygous mammalian model system.

BRIEF DESCRIPTION OF THE FIGURES AND TABLE

FIGS. 1A, 1B, 1C, 1D, and 1E show the nucleic acid molecule (SEQ ID NO:1) encoding the amino acid sequenc (SEQ ID NO:2) of the mammalian protein. The alignment was produced using MACDNASIS PRO software (Hitachi Software Engineering, South San Francisco Calif.).

FIG. 2 shows the alignment between SEQ ID NO:1 and SEQ ID NO:17 (mouse lung PC-TP; GI 897786) produced using the MEGALIGN program (DNASTAR, Madison Wis.).

Table 1 shows the Incyte clones from human and rat which have homology with SEQ ID NO:1 and includes their nucleotide length, biological source, region of overlap with SEQ ID NO:1, and percent identity with SEQ ID NO:1.

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"PTP" refers to a substantially purified protein obtained from any mammalian species, including murine, bovine, ovine, porcine, rodent, canine, simian, and preferably the human species, and from any source, whether natural, synthetic, semi-synthetic, or recombinant.

"Biologically active" refers to a protein having structural, immunological, regulatory, or chemical functions of a naturally occurring, recombinant or synthetic molecule.

"Complementary" refer to the natural hydrogen bonding by base pairing between purines and pyrimidines. For example, the sequence A-C-G-T forms hydrogen bonds with its complements T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a nucleic acid molecule or protein sequence. Chemical modifications of a molecule can include replacement of hydrogen by an alkyl, acyl, or amino group or glycosylation, pegylation, or any similar process which retains or enhances biological activity or lifespan of the molecule.

"Fragment" refers to an Incyte clone or any part of a nucleic acid molecule which retains a usable, functional characteristic. Useful fragments include oligonucleotides which may be used in hybridization or amplification technologies or in regulation of replication, transcription or translation.

"Hybridization complex" refers to a complex between two nucleic acid molecules by virtue of the formation of hydrogen bonds between purines and pyrimidines.

"Ligand" refers to any molecule or compound which will bind to a complementary site on a nucleic acid molecule or protein.

"Modulates" refers to a change in activity (biological, chemical, or immunological) or lifespan resulting from specific binding between a molecule or compound (i.e., ligand) and either a nucleic acid molecule or a protein.

The term "molecules" is used substantially interchangeably with the terms agents and compounds. Such molecules modulate the activity of nucleic acid molecules or proteins of the invention and may be composed of at least one of the following: inorganic and organic substances including nucleic acids, proteins, carbohydrates, fats, and lipids.

"Nucleic acid molecule" refers to a nucleic acid, oligonucleotide, nucleotide, polynucleotide or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded.

"Protein" refers to an amino acid, amino acid sequence, oligopeptide, peptide, or polypeptide or portions thereof whether naturally occurring or synthetic.

"Portion", as used herein, refers to any part of a protein used for any purpose, but especially for the screening of a library of molecules which specifically bind to that portion or for the production of antibodies.

"Sample" is used in its broadest sense. A sample containing nucleic acids may comprise a bodily fluid; an extract from a cell, chromosome, organelle, or membrane isolated from a cell; genomic DNA, RNA, or cDNA in solution or bound to a substrate; a cell; a tissue; a tissue print; and the like.

Molecules or compounds which "specifically bind" the mammalian nucleic acid molecule or protein may include, nucleic acids, carbohydrates, lipids, proteins, or any other organic or inorganic molecules or their combinations which stabilize or modulate the activity of the mammalian protein.

"Substantially purified" refers to nucleic acid molecule or amino acid sequences that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

THE INVENTION

The invention is based on the discovery of a new mammalian nucleic acid molecule which encodes a mammalian protein, phospholipid transport protein (PTP), and the use of the nucleic acid molecule, or fragments thereof, and amino acid sequences, or portions thereof, as compositions in the characterization, diagnosis, treatment, or prevention of conditions such as disorders associated with cell proliferation, lipid metabolism and transport.

Nucleic acids encoding the mammalian protein of the present invention were identified by BLAST analysis using Incyte clone number 700137522 (SEQ ID NO:15) from the rat liver library (RALINOT01) which was differentially expressed in male rat reproductive tissue. A consensus sequence, SEQ ID NO:1, was assembled from the following overlapping and/or extended nucleic acid fragments found in Incyte Clones 3591822F6, 745516R6, 1807728F6, 1772859H1, 1505466H1, 798614H1, 4114738H1, 1923871H1, and 2013709H1; SEQ ID NOs:3–11, respectively. FIGS. 1A, 1B, 1C, 1D, and 1E show the consensus sequence and translation of SEQ ID NO:1.

In one embodiment, the protein comprising the amino acid sequence of SEQ ID NO:2, PTP, is 291 amino acids in length and has three potential N-glycosylation sites at residues N44, N147, and N201; four potential casein kinase II phosphorylation sites at residues S35, T81, S271, and S284; and four potential protein kinase C phosphorylation sites at residues S32, S118, T132, and S149. The oligopeptides from residue H66 to residue A79 or from residue L82 to residue S97 of SEQ ID NO:2, are useful for purifying a ligand or for antibody production. The protein has chemical and structural similarity with mouse lung PC-TP (GI 897786; SEQ ID NO:17). In particular, as shown in FIG. 2, PTP and the mouse lung PC-TP protein share 31% identity and 52% similarity from residue H66 through residue Y222 of PTP (FIG. 2).

Table 1 shows the nucleic acid fragments from human and rat and their sequence coverage and identity with SEQ ID NO:1. Columns 1 and 2 list the SEQ ID NO and Incyte clone number, respectively, for each nucleic acid fragment. The fragments of SEQ ID NO:1, SEQ ID NOs:3–11, are useful in hybridization or amplification technologies to identify and distinguish between the mammalian protein disclosed herein and similar sequences including SEQ ID NOs: 12–16. Column 3 lists the nucleotide length for each fragment. Columns 4 and 5 identify the source organism and Incyte cDNA library from which the fragments were isolated, respectively. Column 6 identifies the range of nucleotide residues in SEQ ID NO:1 over which each fragment shows identity. Column 7 shows the percent sequence identity between each fragment and SEQ ID NO:1 over the nucleotides set forth in column 6.

The mammalian fragments comprising SEQ ID NO:12–16 from rat, were identified using either SEQ ID NO:1 or one of the Incyte clones, SEQ ID NOs:3–11. Any of these sequences may be used in hybridization and amplification technologies to identify and distinguish between SEQ ID NO:1 and similar sequences in a sample. The sequences may be used to produce transgenic animal models which mimic human conditions, diseases, or disorders or to monitor animal toxicology studies, clinical trials, and subject/patient treatment profiles. Northern analysis shows expression of this sequence in various libraries, particularly reproductive (32%), gastrointestinal (28%), and nervous (15%) tissues. SEQ ID NO:1 has a 70% association with cancerous or proliferating tissues and a 22% association with inflamed, immune responsive, or infected tissues. Of particular note is the expression of PTP in libraries and under conditions associated with cell proliferation, lipid metabolism and transport.

Characterization and Use of the Invention
cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequence was chemically and/or electronically assembled from fragments including Incyte clones, extension, and/or shotgun sequences using computer programs such the AUTOASSEMBLER application (PE Biosystems, Foster City Calif.).

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase, thermostable T7 DNA polymerase (Amersham Pharmacia Biotech, Piscataway N.J.), or combinations of polymerases and proofreading exonucleases such as those found in the ELONGASE amplification system (Life Technologies, Rockville Md. Preferably, sequence preparation is automated with machines such as the HYDRA microdispenser (Robbins Scientific, Sunnyvale Calif.), MICROLAB 2200 (Hamilton, Reno Nev.), and the DNA ENGINE thermal cycler (PTC200; MJ Research, Watertown Mass.). Machines used for sequencing include the ABI 3700, 377 or 373 DNA sequencing systems (PE Biosystems), the MEGABACE 1000 DNA sequencing system (Amersham Pharmacia Biotech), and the like. The sequences may be analyzed using a variety of algorithms which are well known in the art and described in Ausubel (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative of regions flanking the nucleic acid molecules of interest. Prefinished sequences (incomplete assembled sequences) are inspected for identity using various algorithms or programs well known in the art, CONSED (Gordon (1998) Genome Res. 8:195–202). Contaminating sequences including vector or chimeric sequences or deleted sequences can be removed or restored, respectively, organizing the prefinished sequences into finished sequences.

Extension of the Nucleic Acid Sequence

The sequences of the invention may be extended using various PCR-based methods known in the art. For example, the XL-PCR kit (PE Biosystems), nested primers, and commercially available cDNA or genomic DNA libraries (Life Technologies; Clontech, Palo Alto Calif., respectively) may be used to extend the nucleotide sequence. For all PCR-based methods, primers may be designed using commercially available software, such as OLIGO 4.06 Primer Analysis software (National Biosciences, Plymouth Minn.) to be about 22 to 30 nucleotides in length, to have a GC content of about 50% or more, and to anneal to a target sequence at temperatures from about 55° C. to about 68° C. When extending a sequence to recover regulatory elements, it is preferable to use genomic, rather than cDNA libraries.

USE OF THE MAMMAL1AN NUCLEIC ACID MOLECULE

Hybridization

The nucleic acid molecule of SEQ ID NO:1 and fragments thereof can be used in various hybridization technologies for various purposes. Hybridization probes may be designed or derived from SEQ ID NO:1. Such probes may be made from a highly specific region such as the 5' regulatory region or from a conserved motif, and used in protocols to identify naturally occurring molecules encoding the mammalian protein, allelic variants, or related molecules, and should preferably have at least 50% amino acid sequence identity to any of the protein sequences. The hybridization probes of the subject invention may be DNA or RNA and may be derived from the molecule of SEQ ID NO:1 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid molecule may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are completely complementary. In some membrane-based hybridizations, perferably 35% or most preferably 50%, formamide can be added to the hybridization solution to reduce the temperature at which hybridization is performed, and background signals can be reduced by the use of other detergents such as Sarkosyl or Triton X-100 (Sigma-Aldrich,St. Louis Mo.)and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application WO95/251116; Shalon et al. (1995) PCT application WO95/35505; Heller et al. (1997) Proc. Natl. Acad. Sci. 94:2150–2155; and Heller et al. (1997) U.S. Pat. No. 5,605,662.)

Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome DNA libraries.

Expression

A multitude of nucleic acid molecules capable of encoding the mammalian protein may be cloned into a vector and used to express the protein, or portions thereof, in host cells. The nucleotide sequence can be engineered by such methods as DNA shuffling (Stemmer and Crameri (1996) U.S. Pat. No. 5,830,721 incorporated by reference herein) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and 3' untranslated regions) from various sources which have been selected for their efficiency in a particular host. The vector, nucleic acid sequence, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. Sequences may be ligated into the E1 or E3 region of the viral genome, and the infective virus used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian nucleic acid molecule is based on DNA—DNA or DNA—RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20). Automated synthesis may also be carried out on machines such as the ABI 431 A Peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties*, WH Freeman, New York N.Y.).

Preparation and Screening of Antibodies

Various hosts including goats, rabbits, rats, mice, humans, and others may be immunized by injection with mammalian protein or any portion thereof. Adjuvants such as Freund's, mineral gels, and surface active substances such as lysolecithin, pluronic polyols, polyanions, peptides, oil emulsions, keyhole limpet hemocyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol. Methods 81:31–42; Cote et al. (1983) Proc. Natl. Acad. Sci. 80:2026–2030; and Cole et al. (1984) Mol. Cell Biol. 62:109–120.)

Alternatively, techniques described for the production of single chain antibodies may be adapted, using methods known in the art, to produce epitope specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The mammalian protein may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP (Amersham Pharmacia Biotech) or amino acid such as $^{35}$S-methionine (USB, Cleveland Ohio). Nucleic acids and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

DIAGNOSTICS

The nucleic acid molecules, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Conditions, diseases or disorders associated with altered expression include actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandboff's disease, hyperlipidemia, hyperlipemia, lipid myopathies, obesity, akinesia, amyotrophic lateral sclerosis, ataxia telangiectasia, cystic fibrosis, Becker's muscular dystrophy, Bell's palsy, Charcot-Marie Tooth disease, diabetes mellitus, diabetes insipidus, diabetic neuropathy, Duchenne muscular dystrophy, byperkalemic periodic paralysis, normokalemic periodic paralysis, Parkinson's disease, malignant hyperthermia, multidrug resistance, myasthenia gravis, myotonic dystrophy, catatonia, tardive dyskinesia, dystonias, peripheral neuropathy, cerebral neoplasms; cardiac disorders associated with transport, e.g., angina, bradyarrythmia, tachyarrythmia, hypertension, Long QT syndrome, myocarditis, cardiomyopathy, nemaline myopathy, centronuclear myopathy, lipid myopathy, mitochondrial myopathy, thyrotoxic myopathy, ethanol myopathy, dermatomyositis, inclusion body is myositis, infectious myositis, polymyositis; neurological disorders associated with transport, e.g., Alzheimer's disease, amnesia, bipolar disorder, dementia, depression, epilepsy, Tourette's disorder, paranoid psychoses, and schizophrenia; and other disorders associated with transport, e.g., neurofibromatosis, postherpetic neuralgia, trigeminal neuropathy, sarcoidosis, sickle cell anemia, Wilson's disease, cataracts, infertility, pulmonary artery stenosis, sensorineural autosomal deafness, hyperglycemia, hypoglycemia, Grave's disease, goiter, Cushing's disease, Addison's disease, glucose-galactose malabsorption syndrome, hypercholesterolemia, adrenoleukodystrophy, Zellweger syndrome, Menkes disease, occipital horn syndrome, von Gierke disease, cystinuria, iminoglycinuria, Hartup disease, Fanconi disease, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

For example, the nucleotide sequence may be labeled by standard methods and added to a biological sample from a patient under conditions for the formation of hybridization complexes. After an incubation period, the sample is washed and the amount of label, or its signal, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a sequence or a fragment thereof under conditions for hybridization or amplification. Standard hybridization may be quantified by comparing the values obtained from normal subjects with values from an experiment in which a known amount of a substantially purified nucleic acid molecule is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology*, Wiley-Interscience, New York N.Y.; and Pound, supra.)

THERAPEUTICS

Chemical and structural similarity, e.g., in the context of sequences and motifs, exists between regions of the PTP and phospholipids from rat. In addition, gene expression is closely associated with reproductive, gastrointestinal, and nervous tissues and appears to play a role in conditions such as disorders associated with cell proliferation, lipid metabolism and transport. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, lipid myopathies, obesity, akinesia, amyotrophic lateral sclerosis, ataxia telangiectasia, cystic fibrosis, Becker's muscular dystrophy, Bell's palsy, Charcot-Marie Tooth disease, diabetes mellitus, diabetes insipidus, diabetic neuropathy, Duchenne muscular dystrophy, hyperkalemic periodic paralysis, normokalemic periodic paralysis, Parkinson's disease, malignant hyperthermia, multidrug resistance, myasthenia gravis, myotonic dystrophy, catatonia, tardive dyskinesia, dystonias, peripheral neuropathy, cerebral neoplasms; cardiac disorders associated with transport, e.g., angina, bradyarrythmia, tachyarrythmia, hypertension, Long QT syndrome, myocarditis, cardiomyopathy, nemaline myopathy, centronuclear myopathy, lipid myopathy, mitochondrial myopathy, thyrotoxic myopathy, ethanol myopathy, dermatomyositis, inclusion body myositis, infectious myositis, polymyositis; neurological disorders associated with transport, e.g., Alzheimer's disease, amnesia, bipolar disorder, dementia, depression, epilepsy, Tourette's disorder, paranoid psychoses, and schizophrenia; and other disorders associated with transport, e.g., neurofibromatosis, postherpetic neuralgia, trigeminal neuropathy, sarcoidosis, sickle cell anemia, Wilson's disease, cataracts, infertility, pulmonary artery stenosis, sensorineural autosomal deafness, hyperglycemia, hypoglycemia, Grave's disease, goiter, Cushing's disease, Addison's disease, glucose-galactose malabsorption syndrome, hypercholesterolemia, adrenoleukodystrophy, Zellweger syndrome, Menkes disease, occipital horn syndrome, von Gierke disease, cystinuria, iminoglycinuria, Hartup disease, Fanconi disease, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising a substantially purified mammalian protein in conjunction with a pharmaceutical carrier may be administered to a subject to treat or prevent a condition associated with altered lifespan, expression, or activity of the mammalian protein including, but not limited to, those provided above.

In a further embodiment, a ligand which modulates the activity of the mammalian protein may be administered to a subject to treat or prevent a condition associated with altered lifespan, expression, or activity of the protein including, but not limited to, those listed above. In one aspect, an antibody which specifically binds the mammalian protein may be used as a targeting or delivery mechanism for bringing a pharmaceutical agent to cells or tissue which express the mammalian protein.

In an additional embodiment, a vector capable of expressing the mammalian protein or a portion or derivative thereof may be administered to a subject to treat or prevent a condition associated with altered lifespan, expression, or activity of protein including, but not limited to, those described above.

In a still further embodiment, a vector expressing the complement of the nucleic acid molecule or fragments thereof may be administered to a subject to treat or prevent a condition associated with altered lifespan, expression, or activity of the protein including, but not limited to, those described above.

Any of the nucleic acids molecules or fragments thereof or proteins or portions thereof, vectors delivering these molecules, and their ligands may be administered in combination with other therapeutic agents. Selection of the agents for use in combination therapy may be made by one of ordinary skill in the art according to conventional pharmaceutical principles. A combination of therapeutic agents may act synergistically to effect prevention or treatment of a particular condition at a lower dosage of each agent.

Modification of Gene Expression Using Nucleic Acids

Gene expression may be modified by designing complementary sequences or antisense molecules (DNA, RNA, or PNA) to the control, 5', 3' or regulatory regions of the mammalian gene. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177.) A complementary sequence may also be designed to block translation by preventing binding between ribosomes and mRNA. In one alternative, a library of nucleic acid molecules or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening Assays

The nucleic acid molecule encoding the mammalian protein may be used to screen a library of molecules for specific binding affinity. The assay can be used to screen a library of DNA molecules, RNA molecules, PNAs, peptides, or proteins including transcription factors, enhancers, repressors, and the like which modulate or regulate the activity of the nucleic acid molecule in the biological system. The assay involves providing a library of molecules, combining the mammalian nucleic acid molecule or a fragment thereof with the library of molecules under conditions allowing specific binding, and detecting specific binding to identify at least one molecule which specifically binds the nucleic acid molecule.

Similarly, the nucleic acid molecule or a fragment thereof may be used to purify a ligand from a sample (cf. protein example below). A method for using a mammalian protein or a portion thereof to purify a ligand would involve providing a sample, combining the protein with the sample under conditions to allow specific binding, and detecting specific binding, recovering the bound protein, and using an appropriate agent to separate the protein from the purified ligand.

Likewise the mammalian protein or a portion thereof may be used to screen libraries of molecules in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs, and the like, ligands which specifically bind the protein. One method for high throughput screening using very small assay volumes and very small amounts of test compound is described in U.S. Pat. No. 5,876,946, incorporated herein by reference, which screens large numbers of molecules for enzyme inhibition or receptor binding. Similarly, the protein or a portion thereof may be used to purify a ligand from a sample. A method for using a mammalian protein or a portion thereof to purify a ligand would involve providing a sample, combining the protein or a portion thereof with the sample under conditions to allow specific binding, detecting specific binding between the protein and ligand, recovering the bound protein, and using an appropriate agent to separate the protein from the purified ligand.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

MODEL SYSTEMS

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A rodent strain inbred to over-express a particular gene may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle which produces the number of organisms needed to satisfy statistical requirements.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transzenic Animal Models

Transgenic rodents which over-express or under-express a gene of interest may be inbred and used to model human diseases or to test therapeutic or toxic agents. (See U.S. Pat. No. 4,736,866; U.S. Pat. No. 5,175,383; and U.S. Pat. No. 5,767,337; incorporated herein by reference). In some cases, the introduced gene may be activated at a specific time in a specific tissue type during fetal development or postnatally. Expression of the transgene is monitored by analysis of phenotype, tissue-specific mRNA expression, and challenged with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene sequence which disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Then transformed ES cells are selected under conditions, identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168:342–357; Wiles and Keller (1991) Development 111:259–267; and Klug et al. (1996) J. Clin. Invest. 98:216–224). Recent developments demonstrate that ES cells derived from human blastocysts may also be manipulated in vitro to differentiate into eight separate cell lineages, including endoderm, mesoderm, and ectodermal cell types (Thomson (1998) Science 282:1145–1147).

Knockout Analysis

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc. Natl. Acad. Sci. 95:11371–11376; Baudoin et al. (1998) Genes Dev. 12:1202–1216; and Zhuang et al. (1998) Mol. Cell Biol. 18:3340–3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macacafascicularis, Macaca mulatta*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPS are the first choice test animal. In addition, NHPS and individual humans exhibit differential sensitivities to many drugs and toxins and can be classified as "extensive metabolizers" and "poor metabolizers" of these agents.

In additional embodiments, the nucleic acid molecules which encode the mammalian protein may be used in any molecular biology techniques that have yet to be developed, provided the new techniques rely on properties of nucleic acid sequences that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, the preparation of the human meningioma cDNA library, MENTUNON3, is described.

I Representative cDNA Sequence Preparation

The normalized human meningioma cDNA library MENTUNON3 was constructed from tissue obtained from a 35-year-old Caucasian female during a right suboccipital craniectomy. The frozen tissue was homogenized and lysed in guanidinium isothiocyanate solution using a POLYTRON homogenizer (PT-3000; Brinkmann Instruments, Westbury N.J.). The lysate was centrifuged over a 5.7 M CsCl cushion using an SW28 rotor in an L8–70M ultracentrifuge (Beckman Coulter, Inc., Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNase (Life Technologies) at 37° C. The RNA extraction and precipitation were repeated twice as before.

Messenger RNA (mRNA) was isolated using the OLIGOTEX kit (Qiagen, Valencia Calif.) and used to construct the cDNA library. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors and digested with NotI (New England Biolabs, Beverly Mass.). The cDNAs were fractionated on a SEPHAROSE CL-4B column (Amersham Pharmacia Biotech), and those cDNAs exceeding 400 bp were ligated into the NotI and EcoRI sites of the pINCY plasmid (Incyte Genomics, Palo Alto Calif.). The plasmid was transformed into competent DH5α cells (Life Technologies) or ELECTROMAX DH 10B cells (Life Technologies).

Plasmid DNA was released from the cells and purified using the REAL PREP 96 plasmid kit (Qiagen). The recommended protocol was employed except for the following changes:1) the bacteria were cultured in 1 ml of sterile TERRIFIC BROTH (BD Biosciences, Sparks Md. with carbenicillin at 25 mg/l and glycerol at 0.4%; 2) after inoculation, the cultures were incubated for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using either a MICROLAB 2200 system (Hamilton, Reno Nev.) or a HYDRA microdispenser (Robbins Scientific, Sunnyvale Calif.) in combination with DNA ENGINE thermal cyclers (MJ Research). The cDNAs were sequenced by the method of Sanger, F. and A. R. Coulson (1975; J. Mol. Biol. 94:441–448) using either an ABI PRISM 377 (PE Biosystems) or MEGABACE 1000 sequencing system (Amersham Pharmacia Biotech). Most of the isolates were sequenced using standard ABI protocols and kits (PE Biosystems) with solution volumes of 0.25× –1.0× concentrations. In the alternative, cDNAs were sequenced using solutions and dyes from Amersham Pharmacia Biotech.

II Identification, Extension, Assembly, and Analyses of the Sequences

Incyte clone 700137522(SEQ ID NO:15) from the ZOOSEQ database (Incyte Genomics) of rat cDNA sequences was, identified during analysis of differential expression of sequences in male reproductive tissues. Incyte clone 700137522 was used to identify first pass and extended cDNAs in the LIFESEQ database (Incyte Genomics), SEQ ID Nos:3–11, which were assembled using Phrap (Green, University of Washington). The assembled sequence, SEQ ID NO:1 was translated using MACDNASIS PRO software (Hitachi Software Engineering) to elucidate the coding region, SEQ ID NO:2. The nucleotide and amino acid sequences were queried against databases such as the GenBank databases, SwissProt, BLOCKS, PRINTS, Prosite, and PFAM using BLAST. Motif and HMM algorithms were used to perform functional analyses, and the antigenic index (Jameson-Wolf analysis) was determined using LASERGENE software (DNASTAR). Then, the clones and assembled sequence were compared using BLAST across all mammalian libraries to identify homologous nucleic acid sequences, SEQ ID NOs:12–16.

III Sequence Similarity

Sequence similarity was calculated as percent identity based on comparisons between at least two nucleic acid or amino acid sequences using the clustal method of the MEGALIGN program (DNASTAR). The clustal method uses an algorithm which groups sequences into clusters by examining the distances between all pairs. After the clusters are aligned pairwise, they are realigned in groups. Percent similarity between two sequences, sequence A and sequence B, is calculated by dividing the length of sequence A, minus the number of gap residues in sequence A, minus the number of gap residues in sequence B, into the sum of the residue matches between sequence A and sequence B, times one hundred. Gaps of very low or zero similarity between the two sequences are not included.

IV Northern Analysis

Northern analysis is a laboratory technique used to detect the presence of a transcript of a gene and involves the hybridization of a labeled probe to a membrane on which RNAs from a particular cell type or tissue have been bound.

Analogous computer techniques applying BLAST were used to search for identical or related molecules in nucleotide databases such as GenBank or LIFESEQ (Incyte Genomics). Sequence-based analysis is much faster than membrane-based hybridization, and the sensitivity of the computer search can be modified to determine whether any particular match is categorized as exact or similar. The basis of the search is the product score which is defined as: (percent sequence identity x percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a percentage distribution of libraries in which the transcript encoding the mammalian protein occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries across all categories.

V Extension of Nucleic Acid Sequences

The nucleic acid sequence of SEQ ID NO:1 was produced by assembly of first pass and extended clones. At least one of the Incyte cDNA clones was extended using oligonucleotide primers; one primer was synthesized to initiate 5' extension of the known fragment, and the other, to initiate 3' extension of the known fragment. The initial primers were designed using OLIGO 4.06 software (National Biosciences) to be about 22 to 30 nucleotides in length, to have a GC content of about 50%, and to anneal to the target sequence at temperatures of about 55°C. to about 68° C. Any fragment which would result in hairpin structures and primer-primer dimerizations was avoided. Selected human cDNA libraries were used to extend the sequence. If more than one extension is needed, additional or nested sets of primers are designed.

High fidelity amplification was obtained by performing PCR in 96-well plates using the PTC-200 (MJ Research). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair selected from the plasmid: Step 1:94° C., 3 min; Step 2: 94° C., 15 sec; Step 3: 60° C., 1 min; Step 4: 68° C., 2 min; Step 5: Steps 2, 3, and 4 repeated 20 times; Step 2: 68° C., 5 min; Step 7: storage at 4° C. In the alternative, parameters for the primer pair, T7 and SK+ (Stratagene), were as follows: Step 1: 94° C., 3 min; Step 2: 94° C., 15 sec; Step 3: 57° C., 1 min; Step 4; 68° C., 2 min; Step 5: Steps 2, 3, and 4 repeated 20 times; Step 7: storage at 4° C.

The concentration of DNA in each well was determined by dispensing 100 µl PICOGREEN quantitation reagent (0.25% (v/v); Molecular Probes, Eugene Oreg.) dissolved in 1×TE and 0.5 µl of undiluted PCR product into each well of an opaque fluorimeter plate (Corning Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments were separated on about 0.6–0.8% agarose gels, fragments were excised as visualized under UV light, and agar removed/digested with AGARACE (Promega). Extended fragments were religated using T4 DNA ligase (New England Biolabs, Beverly Mass.) into pUC 18 vector (Amersham Pharmacia Biotech), treated with Pfu DNA polymerase (Stratagene) to fill-in restriction site overhangs, and transformed into competent E. coli cells. Transformed cells were selected on antibiotic-containing media, and individual colonies were picked and cultured overnight at 37° C. in 384-well plates in LB/2×carbenicillin liquid media.

The cells were lysed, and DNA was amplified using Taq DNA polymerase (Amersham Pharmacia Biotech) and Pfu DNA polymerase (Stratagene) with the following parameters: Step 1: 94 ° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (PE Biosystems).

In like manner, the nucleotide sequence of SEQ ID NO:1 is used to obtain regulatory sequences using the procedure above, oligonucleotides designed for outward extension, and a genomic DNA library.

VI Labeling of Probes and Hybridization Analyses

Substrate Preparation

Nucleic acid sequences are isolated from a biological source and applied to a substrate for standard nucleic acid hybridization protocols by one of the following methods. A mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20× saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 beads (Amersham Pharmacia Biotech). Purified target nucleic acids are robotically arrayed onto a glass microscope slide (Corning Science Products, Corning N.Y.). The slide is previously coated with 0.05% aminopropyl silane (Sigma-Aldrich, St. Louis Mo.) and cured at 110°C. The arrayed glass slide (microarray) is exposed to UV irradiation in a STRATALINKER UV-crosslinker (Stratagene).

Probe Preparation cDNA probe sequences are made from mRNA templates. Five micrograms of mRNA is mixed with 1 μg random primer (Life Technologies), incubated at 70° C. for 10 minutes, and lyophilized. The lyophilized sample is resuspended in 50 μl of 1× first strand buffer (cDNA Synthesis systems; Life Technologies) containing a dNTP mix, [α-$^{32}$P] dCTP, dithiothreitol, and MMLV reverse transcriptase (Stratagene), and incubated at 42° C. for 1–2 hours. After incubation, the probe is diluted with 42 μl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 Micro-Column (Amersham Pharnacia Biotech). Probes can be labeled with fluorescent markers, Cy3-dCTP or Cy5-dCTP (Amersham Pharmacia Biotech), in place of the radionuclide, [$^{32}$P]dCTP.

Hybridization

Hybridization is carried out at 65° C. in a hybridization buffer containing 0.5 M sodium phosphate (pH 7.2), 7% SDS, and I mM EDTA. After the substrate is incubated in hybridization buffer at 65° C. for at least 2 hours, the buffer is replaced with 10 ml of fresh buffer containing the probe sequences. After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the substrate is examined by confocal laser microscopy, and images are collected and analyzed using GEMTOOLS gene expression analysis software (Incyte Genomics).

VII Complementary Nucleic Acid Sequences

Sequences complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or their derivatives (PNAs). Oligonucleotides are designed using OLIGO 4.06 software (National Biosciences) and SEQ ID NO:1 or its fragments, SEQ ID NOs:3–11. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

VIII Expression of the Mammalian Protein

Expression and purification of the mammalian protein are achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera frugiperda* (Sf9) insect cells with recombinant baculovirus, *Autographica californica* nuclear polyhedrosis virus. The polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., glutathione S-transferase (GST) or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity (Amersham Pharmacia Biotech). Following purification, the GST moiety can be proteolytically cleaved from the mammalian protein at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (Q1AGEN). Methods for protein expression and purification are discussed in Ausubel (supra, unit 16). Purified mammalian protein obtained by these methods can be used directly in the following activity assay.

IX Functional Assays

Protein function is assessed by expressing the sequences encoding PTP at physiologically elevated levels in mammalian cell culture. The nucleic acid sequence is subcloned into PCMV SPORT vector (Life Technologies), which contains the strong cytomegalovirus promoter, and 5–10 μg of the vector is transformed into a endothelial or hematopoietic human cell line using transformation methods well known in the art. An additional 1–2 μg of a plasmid containing sequence encoding CD64-GFP (Clontech) is co-transformed to provide an fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells is separated using magnetic beads coated with either human IgG or antibody against CD64 (DYNAL, Lake Success N.Y.). mRNA is purified from the cells and analyzed by hybridization techniques.

X Production of PTP Specific Antibodies

PTP is purified using polyacrylamide gel electrophoresis and used to immunize rabbits. Antibodies are produced using protocols well known to those skilled in the art.

Alternatively, the amino acid sequence of PTP is analyzed using LASERGENE software (DNASTAR) to determine regions of high immunogenicity. An immunogenic epitope, usually found near the C-terminus or in a hydrophilic region is selected, synthesized, and used to raise antibodies by means known to those of skill in the art.

Typically, epitopes of about 15 residues in length are produced using an ABI 43 1A Peptide synthesizer (PE Biosystems) using Fmoc-chemistry and coupled to KLH (Sigma-Aldrich) by reaction with N-maleimidobenzoyl-N-hydroxysuccinimide ester to increase immunogenicity. Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XI Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersham Pharmacia Biotech). Media containing the protein is passed over the immunoaffinity column, and the column is washed using high ionic strength buffers in the presence of detergent to allow preferential absorbence of the protein. After coupling, the column is eluted using a buffer of pH 2–3 or a high concentration of urea or thiocyanate ion to disrupt antibody/protein binding, and the protein is collected.

XII Screening Molecules for Specific Binding with the Nucleic Acid Molecule or Protein The nucleic acid molecule, or fragments thereof, or the protein, or portions thereof, are labeled with $^{32}$P-dCTP, Cy3-dCTP, Cy5-dCTP (Amersham Pharmacia Biotech), or BIODIPY or FITC (Molecular Probes, Eugene Oreg.), respectively. Libraries of candidate molecules previously arranged on a substrate are incubated in the presence of labeled nucleic acid molecule or protein. After incubation under conditions for either a nucleic acid molecule or amino acid sequence, the substrate is washed, and any position on the substrate retaining label, which indicates specific binding or complex formation, is assayed, and the binding molecule is identified. Data obtained using different concentrations of the nucleic acid molecule or protein are used to calculate affinity between the labeled nucleic acid molecule or protein and the bound molecule.

XIII Demonstration of Protein Activity

PTP, or biologically active fragments thereof, are labeled with $^{125}$I Bolton-Hunter reagent ( Bolton et al. (1973) Biochem. J. 133:529). Candidate molecules, including various PC molecular species, previously arrayed in the wells of a multi-well plate are incubated with the labeled PTP, washed, and any wells with labeled PTP complex are assayed. Data obtained using different concentrations of PTP are used to calculate values for the number, affinity, and association of PTP with the candidate molecules.

TABLE 1

| Nucleic Acid SEQ ID NO: | Incyte Clone Number | Nucleotide Length | Source | Library | Coverage | Percent Identity |
|---|---|---|---|---|---|---|
| 3 | 3591822F6 | 573 | Homo sapiens | 293TF5T01 | 1–573 | n/a |
| 4 | 745516R6 | 516 | Homo sapiens | BRAITUT01 | 459–981 | n/a |
| 5 | 1807728F6 | 411 | Homo sapiens | SINTNOT13 | 709–1122 | n/a |
| 6 | 1772859H1 | 248 | Homo sapiens | MENTUNON3 | 924–1171 | n/a |
| 7 | 1505466H1 | 277 | Homo sapiens | BRAITUT07 | 1097–1374 | n/a |
| 8 | 798614H1 | 287 | Homo sapiens | OVARN0T03 | 1112–1398 | n/a |
| 9 | 4114738H1 | 278 | Homo sapiens | UTRSTUT07 | 1333–1615 | n/a |
| 10 | 1923871H1 | 278 | Homo sapiens | BRSTTUT01 | 1393–1668 | n/a |
| 11 | 2013709H1 | 232 | Homo sapiens | TESTNOT03 | 1633–1865 | n/a |
| 12 | 700488211H1 | 289 | Rattus norvegicus | RATENOT01 | 710–1000 | 69.2 |
| 13 | 700607704H1 | 279 | Rattus norvegicus | RALINOH01 | 923–1201 | 87.4 |
| 14 | 701255162H1 | 272 | Rattus norvegicus | RALITXT03 | 1172–1443 | 95.2 |
| 15 | 700137522H1 | 239 | Rattus norvegicus | RALINOT01 | 1387–1669 | 84.9 |
| 16 | 70143S117T1 | 270 | Rattus norvegicus | RALITXT06 | 1585–1859 | 67.8 |

What is claimed is:

1. A substantially purified nucleic acid molecule encoding the protein having the amino acid sequence of SEQ ID NO:2 wherein the protein has phospholipid transfer activity.

2. A fragment of the nucleic acid molecule of claim 1 wherein the fragment is selected from the group consisting of SEQ ID NOs:3–5, 8 and 9 and the complete complements-thereof.

3. The complement of the nucleic acid molecule of claim 1.

4. An expression vector comprising the nucleic acid molecule of claim 1.

5. A method of using a nucleic acid molecule to screen a library of molecules to identify at least one molecule which specifically nucleic acid, the method comprising:
   (a) providing a library of molecules,
   (b) combining the nucleic acid molecule of claim 1 with a library of molecules under conditions to allow specific binding, and
   (c) detecting specific binding, thereby identifying a molecule which specifically binds the nucleic acid molecule.

6. A method of using a nucleic acid molecule to purify a ligand which specifically binds the nucleic acid molecule from a sample, the method comprising:
   (a) providing a sample,
   (b) combining nucleic acid molecule of claim 1 with a sample under conditions to allow specific binding, and
   c) detecting specific binding between the nucleic acid molecule and the ligand,
   d) recovering the bound nucleic acid molecule, and
   e) separating the nucleic acid molecule from the purified ligand, thereby obtaining purified ligand.

7. The complement of a fragment of claim 2.

8. A host cell containing the expression vector of claim 4.

9. The method of claim 5 wherein the library is selected from DNA molecules, RNA molecules, PNAs, peptides, and proteins.

10. A method of producing a protein, the method comprising the steps of:
    (a) culturing a the host cell of claim 8 under conditions for the expression of the protein having the amino acid sequence of SEQ ID NO:2; and
    (b) recovering the protein from the host cell culture.

11. An isolated and purified nucleic acid molecule comprising SEQ ID NO:1 and the complete complement thereof.

12. A method for detecting a nucleic acid molecule in a sample, the method comprising the steps of:
    (a) hybridizing the nucleic acid molecule encoding the protein having the amino acid sequence of SEQ ID NO:2 to at least one nucleic acid in the sample, thereby forming a hybridization complex; and
    (b) detecting the hybridization complex, wherein the presence of the hybridization complex correlates with the presence of the nucleic acid molecule in the sample.

13. The method of claim 12 further comprising amplifying the nucleic acids of the sample prior to hybridization.

* * * * *

UNITED STATES PATENT AND TRADEMARK OFFICE
CERTIFICATE OF CORRECTION

PATENT NO.  : 6,168,933B1
DATED       : January 2, 2001
INVENTOR(S) : Matthew R. Kaser, Jennifer L. Hillman, Mariah R. Baughn It is certified that error appears in the above-identified patent and that said Letters Patent is hereby corrected as shown below:

Column 39,
Line 45, insert -- binds the -- before "nucleic acid,";

Column 40,
Line 42, delete "a the host cell" and insert -- the host cell --.

Signed and Sealed this

Thirty-first Day of July, 2001

Attest:

NICHOLAS P. GODICI
Attesting Officer  Acting Director of the United States Patent and Trademark Office

SEQUENCE LISTING

<160> NUMBER OF SEQ ID NOS:   17

<210> SEQ ID NO 1
<211> LENGTH: 1865
<212> TYPE: DNA
<213> ORGANISM: Homo sapiens
<220> FEATURE: -

<223> OTHER INFORMATION: 1772859CB1

<400> SEQUENCE: 1

| | | | | | |
|---|---|---|---|---|---|
| atcgttctgt | ggtcctttct | tttatgattc | acaaggaatg | accctcttca | tcgcctctcc | 60 |
| taattcagtc | ctcacaacag | tccttttaca | aatgggacaa | caggttagag | gaagtcaggc | 120 |
| agatttccag | catcatagag | agtaaaggac | cagggaagga | tcaggattca | aggactgcac | 180 |
| ccaggctctg | cttccagctt | gctgtgtgac | tttgggtaat | tttgttccct | tagggaactg | 240 |
| agctttctca | tttgtaaatg | caaacaggct | gttgggagga | tcaaatgaga | tccaggggtg | 300 |
| aaaacagctt | agtttacttt | caggaattta | cccacgcggt | atataaaggc | aaaatattat | 360 |
| tatagtcagg | tgattgtaga | ttgaggaacc | catttcctca | tcctgcaaat | tgcaaacctg | 420 |
| agggcccaaa | gagggacagg | ggcttgcccc | aggtctcagc | aggctgtgag | caagagctaa | 480 |
| agcctaatcc | tcctgccttt | gggcctggag | ccttccttg | tacccaggg | gtcagtgtct | 540 |
| ttgttggata | caggcttaga | ttgactgact | gtaccctgag | aacctagggg | agtccctgtt | 600 |
| cccaattctt | ctcctacccc | caccttggcc | tgatggagga | agaccctgct | gtgttgagat | 660 |
| gagcaccaga | gccaagaagc | tgaggaggat | ctggagaatt | ctggaggaag | aggagagtgt | 720 |
| tgctggagct | gtacagaccc | tgcttctcag | gtcccaggaa | ggtggcgtca | gcatctgcag | 780 |
| ccgcgtcgac | gttgtcggag | cctccgcgga | ggacccagga | gagccggact | aggaccaggg | 840 |
| ccctgggcct | ccccacactc | cccatggaga | agctggcggc | ctctacagag | ccccaagggc | 900 |
| ctcggccggt | cctgggccgt | gagagtgtcc | aggtgcccga | tgaccaagac | tttcgcagct | 960 |
| tccggtcaga | gtgtgaggct | gaggtgggct | ggaacctgac | ctatagcagg | gctggggtgt | 1020 |
| ctgtctgggt | gcaggctgtg | gagatggatc | ggacgctgca | caagatcaag | tgccggatgg | 1080 |
| agtgctgtga | tgtgccagcc | gagacactct | acgacgtcct | acacgacatt | gagtaccgca | 1140 |
| agaaatggga | cagcaacgtc | attgagactt | ttgacatcgc | ccgcttgaca | gtcaacgctg | 1200 |
| acgtgggcta | ttactcctgg | aggtgtccca | agcccctgaa | gaaccgtgat | gtcatcaccc | 1260 |
| tccgctcctg | gctccccatg | ggcgctgatt | acatcattat | gaactactca | gtcaaacatc | 1320 |
| ccaaataccc | acctcggaaa | gacttggtcc | gagctgtgtc | catccagacg | ggctacctca | 1380 |
| tccagagcac | agggcccaag | agctgcgtca | tcacctacct | ggcccaggtg | gaccccaaag | 1440 |
| gctccttacc | caagtgggtg | gtgaataaat | cttctcagtt | cctggctccc | aaggccatga | 1500 |
| agaagatgta | caaggcgtgc | ctcaagtacc | ccgagtggaa | acagaagcac | ctgcctcact | 1560 |
| tcaagccgtg | gctgcacccg | gagcagagcc | cgttgccgag | cctggcgctg | tcggagctgt | 1620 |
| cggtgcagca | tgcggactca | ctggagaaca | tcgacgagag | cgcggtggcc | gagagcagag | 1680 |
| aggagcggat | gggcggcgcg | gcggcgagg | gcagcgacga | cgacacctcg | ctcacctgag | 1740 |
| cgccgcaccg | cttcagggac | ggagacagga | ccgggcgagc | cctggggcgg | cggccgctcc | 1800 |
| tgcactttct | cccctcccc | acccggcacc | tggtggcacc | gggccaggcc | caggcgggtg | 1860 |
| ctgca | | | | | | 1865 |

<210> SEQ ID NO 2
<211> LENGTH: 291
<212> TYPE: PRT
<213> ORGANISM: Homo sapiens
<220> FEATURE: -
<223> OTHER INFORMATION: 1772859CD1

<400> SEQUENCE: 2

Met Glu Lys Leu Ala Ala Ser Thr Glu Pro Gln Gly Pro Arg Pro

```
  1               5                   10                  15
Val Leu Gly Arg Glu Ser Val Gln Val Pro Asp Gln Asp Phe
                 20                  25                  30
Arg Ser Phe Arg Ser Glu Cys Glu Ala Glu Val Gly Trp Asn Leu
                 35                  40                  45
Thr Tyr Ser Arg Ala Gly Val Ser Val Trp Val Gln Ala Val Glu
                 50                  55                  60
Met Asp Arg Thr Leu His Lys Ile Lys Cys Arg Met Glu Cys Cys
                 65                  70                  75
Asp Val Pro Ala Glu Thr Leu Tyr Asp Val Leu His Asp Ile Glu
                 80                  85                  90
Tyr Arg Lys Lys Trp Asp Ser Asn Val Ile Glu Thr Phe Asp Ile
                 95                 100                 105
Ala Arg Leu Thr Val Asn Ala Asp Val Gly Tyr Tyr Ser Trp Arg
                110                 115                 120
Cys Pro Lys Pro Leu Lys Asn Arg Asp Val Ile Thr Leu Arg Ser
                125                 130                 135
Trp Leu Pro Met Gly Ala Asp Tyr Ile Ile Met Asn Tyr Ser Val
                140                 145                 150
Lys His Pro Lys Tyr Pro Pro Arg Lys Asp Leu Val Arg Ala Val
                155                 160                 165
Ser Ile Gln Thr Gly Tyr Leu Ile Gln Ser Thr Gly Pro Lys Ser
                170                 175                 180
Cys Val Ile Thr Tyr Leu Ala Gln Val Asp Pro Lys Gly Ser Leu
                185                 190                 195
Pro Lys Trp Val Val Asn Lys Ser Ser Gln Phe Leu Ala Pro Lys
                200                 205                 210
Ala Met Lys Lys Met Tyr Lys Ala Cys Leu Lys Tyr Pro Glu Trp
                215                 220                 225
Lys Gln Lys His Leu Pro His Phe Lys Pro Trp Leu His Pro Glu
                230                 235                 240
Gln Ser Pro Leu Pro Ser Leu Ala Leu Ser Glu Leu Ser Val Gln
                245                 250                 255
His Ala Asp Ser Leu Glu Asn Ile Asp Glu Ser Ala Val Ala Glu
                260                 265                 270
Ser Arg Glu Glu Arg Met Gly Gly Ala Gly Gly Glu Gly Ser Asp
                275                 280                 285
Asp Asp Thr Ser Leu Thr
                290
```

<210> SEQ ID NO 3
<211> LENGTH: 573
<212> TYPE: DNA
<213> ORGANISM: Homo sapiens
<220> FEATURE: -
<223> OTHER INFORMATION: 3591822F6

<400> SEQUENCE: 3

```
atcgttctgt ggtcctttct tttatgattc acaaggaatg accctcttca tcgcctctcc      60
taattcagtc ctcacaacag tccttttaca aatgggacaa caggttagag gaagtcaggc     120
agatttccag catcatagag agtaaaggac cagggaagga tcaggattca aggactgcac     180
ccaggctctg cttccagctt gctgtgtgac tttgggtaat tttgttccct tagggaactg     240
agctttctca tttgtaaatg caaacaggct gttggggagga tcaaatgaga tccaggggtg     300
```

-continued

```
aaaacagctt agtttacttt caggaattta cccacgcggt atataaaggc aaatatattat    360 tatagtcagg tgattgtaga ttgaggaacc catttcctca ttctgcaaat tgcaaacctg    420
agggcccaaa gagggacagg ggcttgcccc aagtctcagc aggctgtgag caagagctaa    480
agcctaatcc tcctgccttt gggcctggag cccttccttg taccccaggg gtcagtgtct    540
ttgttggata caggcttaga ttgactgact gta                                 573
```

<210> SEQ ID NO 4
<211> LENGTH: 516
<212> TYPE: DNA
<213> ORGANISM: Homo sapiens
<220> FEATURE: -
<223> OTHER INFORMATION: 745516R6
<221> NAME/KEY: unsure
<222> LOCATION: 46, 312, 351, 373, 453
<223> OTHER INFORMATION: a, t, c, g, or other

<400> SEQUENCE: 4

```
gcaggctgtg agcaagagct aaagcctaat cctcctgcct ttgggnctgg agccttcctt     60
gtaacccagc ggtcagtgtc tttgttggat acaggcttag attgactgac tgtaccctga   120
gaacctaggg gagtccctgt tcccaattct tctcctaccc ccaccttggc ctgatggagg   180
aagaccctgc tgtgttgaga tgagcaccag agccaagaag ctgaggagga tctggagaat   240
tctggaggaa gaggagagtg ttgctggagc tgtacagacc ctgcttctca ggtcccagga   300
aggtggcgtc anatctgcag ccgcgtcgac gttgtcggag cctccgcgga ngaccccagg   360
agagccggac tangaccagg gccttgggct tcccaacttc ccatggagaa gctggcgggc   420
ttaagagccc aagggctcgc cgtctggcgt aanttcagtg ccatacaact tgagttcgta   480
attagtagtg tgactactta aggtggtttt tgtagc                             516
```

<210> SEQ ID NO 5
<211> LENGTH: 411
<212> TYPE: DNA
<213> ORGANISM: Homo sapiens
<220> FEATURE: -
<223> OTHER INFORMATION: 1807728F6
<221> NAME/KEY: unsure
<222> LOCATION: 63, 396, 406-408, 410
<223> OTHER INFORMATION: a, t, c, g, or other

<400> SEQUENCE: 5

```
ggcaccccgg ccccggcggg ccccggcgga cggcgggcaa aggtcccagg aagtggcgt     60 canatctgca gccgcgtcga cgttgtcgga gcctccgcgg aggacccagg agagccggac   120
taggaccagg gccctgggcc tccccacact ccccatggag aagctggcgg cctctacaga   180
gccccaaggg cctcggccgg tcctgggccg tgagagtgtc caggtgcccg atgaccaaga   240
ctttcgcagc ttccggtcag agtgtgaggc tgaggtgggc tggaacctga cctatagcag   300
ggctggggtg tctgtctggg tgcaggctgt ggagatggat cggacgctgc acaagatcaa   360
gtgccggatg gagtgctgtg atgtgccagc cgaganatct acgacnnncn a            411
```

<210> SEQ ID NO 6
<211> LENGTH: 248
<212> TYPE: DNA
<213> ORGANISM: Homo sapiens
<220> FEATURE: -
<223> OTHER INFORMATION: 1772859H1

<400> SEQUENCE: 6

```
gagtgtccag gtgcccgatg accaagactt cgcagcttc cggtcagagt gtgaggctga     60
```

```
ggtgggctgg aacctgacct atagcagggc tggggtgtct gtctgggtgc aggctgtgga      120
gatggatcgg acgctgcaca agatcaagtg ccggatggag tgctgtgatg tgccagccga      180
gacactctac gacgtcctac acgacattga gtaccgcaag aaatgggaca gcaacgtcat      240
tgagactt                                                                248
```

```
<210> SEQ ID NO 7
<211> LENGTH: 277
<212> TYPE: DNA
<213> ORGANISM: Homo sapiens
<220> FEATURE: -
<223> OTHER INFORMATION: 1505466H1

<400> SEQUENCE: 7
agccgagaca ctctacgacg tcctacacga cattgagtac cgcaagaaat gggacagcaa       60
cgtcattgag acttttgaca tcgcccgctt gacagtcaac gctgacgtgg gctattactc      120
ctggaggtgt cccaagcccc tgaagaaccg tgatgtcatc accctccgct cctggctccc      180
catgggcgct gattacatca ttatgaacta ctcagtcaaa catcccaaat acccacctcg      240
gaaagattgg tccgagctgt gtccatccag acgggct                                277
```

```
<210> SEQ ID NO 8
<211> LENGTH: 287
<212> TYPE: DNA
<213> ORGANISM: Homo sapiens
<220> FEATURE: -
<223> OTHER INFORMATION: 798614H1
<221> NAME/KEY: unsure
<222> LOCATION: 7, 28, 87, 97, 184, 198, 224, 277
<223> OTHER INFORMATION: a, t, c, g, or other

<400> SEQUENCE: 8
cgacgtncta cacgacattg agtaccgnaa gaaatgggac agcaacgtca ttgagacttt       60
tgacatcgac cgcttgacag tcaacgntga cgtgggntat tactcctgga ggtgtcccaa      120
gcccctgaag aaccgtgatg tcatcaacct tcggttctgg gttccatgg cgctgatta         180 catnattatg aactactnag tcaaacatcc caaataccca cctngaaaag acttggtccg      240
agctgtgtcc atccagacgg ggtacctgat tcagagnaca agggcca                    287
```

```
<210> SEQ ID NO 9
<211> LENGTH: 278
<212> TYPE: DNA
<213> ORGANISM: Homo sapiens
<220> FEATURE: -
<223> OTHER INFORMATION: 4114738H1
<221> NAME/KEY: unsure
<222> LOCATION: 46, 82, 83, 201, 203, 222, 228
<223> OTHER INFORMATION: a, t, c, g, or other

<400> SEQUENCE: 9
ctcggaaaga cttggtccga gctgtgtcca tccagacggg ctaccncatc cagagcacag       60
ggcccaagag ctgcgtcatc annacctggc ccaggtggac cccaaaggct ccttacccaa      120
gtgggtggtg aataaatctt ctcagttcct ggctcccaag gccatgaaga agatgtacaa      180
ggcgtgcctc aagtaccccg ngnggaaaca gaagcacctg gnctcatnca agtgtggctg      240 caccggagc agagcccgtt gccgagcctg gcgctgtc                              278
```

```
<210> SEQ ID NO 10
<211> LENGTH: 278
<212> TYPE: DNA
```

<213> ORGANISM: Homo sapiens
<220> FEATURE: -
<223> OTHER INFORMATION: 1923871H1

<400> SEQUENCE: 10

```
caggcccaag agctgcgtca tcacctacct ggcccaggtg gaccccaaag gctccttacc      60
caagtgggtg gtgaataaat cttctcagtt cctggctccc aaggccatga agaagatgta     120
caaggcgtgc ctcaagtacc ccgagtggaa acagaagcac ctgcctcact tcaagccgtg     180
gctgcacccg gagcagagcc cgttgccgag cctggcgctg tcggagctgt cggtgcagca     240
tgcggactca ctggagaaca tcgacgagag cgcggtgg                            278
```

<210> SEQ ID NO 11
<211> LENGTH: 232
<212> TYPE: DNA
<213> ORGANISM: Homo sapiens
<220> FEATURE: -
<223> OTHER INFORMATION: 2013709H1
<221> NAME/KEY: unsure
<222> LOCATION: 61
<223> OTHER INFORMATION: a, t, c, g, or other

<400> SEQUENCE: 11

```
cggactcact ggagaacatc gacgagagcg cggtggccga gagcagagag gagcggatgg      60
ncggcgcggg cggcgagggc agcgacgacg acacctcgct cacctgagcg ccgcaccgct     120
tcagggacgg agacaggacc gggcgagccc tggggcggcg gccgctcctg cactttctcc     180
cctcccccac ccggcacctg gtggcacggg ccaggcccag gcgggtgctg ca             232
```

<210> SEQ ID NO 12
<211> LENGTH: 289
<212> TYPE: DNA
<213> ORGANISM: Rattus norvegicus
<220> FEATURE: -
<223> OTHER INFORMATION: 700488211H1
<221> NAME/KEY: unsure
<222> LOCATION: 37
<223> OTHER INFORMATION: a, t, c, g, or other

<400> SEQUENCE: 12

```
gacgccacct tcctgggacc tgtacgggct tcttgcnggg gcgggccggg gccggggtgc      60
gagctcttcc gccgcgccga cgttgtctga gcctccgcgg aggacccagg agagtcggac     120
taggaccagg gccccgggcc tccccacgct ctctatggaa aagccagctg cttcaacaga     180
accccaaggg cctcggcccg cttttgggccg tgaaagtgtc caggtgcccg atgaccagga     240
cttccgcagt tttcggtcag agtgtgaggc cgaggtggtg gaacctgac                 289
```

<210> SEQ ID NO 13
<211> LENGTH: 279
<212> TYPE: DNA
<213> ORGANISM: Rattus norvegicus
<220> FEATURE: -
<223> OTHER INFORMATION: 700607704H1

<400> SEQUENCE: 13

```
aagtgtccag gtgcccgatg accaggactt ccgcagtttt cggtcagagt gtgaggccga      60
ggtgggctgg aacctgacct acagcaaggc cggtgtgtct gtgtgggtgc aggctgtgga     120
gatggatcga actctgcaca agatcaagtc caggatggaa tgctgtgacg taccagctga     180
gacgctctac gatgtcctgc acgacataga ataccgaaag aagtgggaca gtaatgtcat     240
cgagacattc gacatcgctc gactgactgt caacgctga                            279
```

<210> SEQ ID NO 14
<211> LENGTH: 272
<212> TYPE: DNA
<213> ORGANISM: Rattus norvegicus
<220> FEATURE: -
<223> OTHER INFORMATION: 701255162H1

<400> SEQUENCE: 14

```
cgacatcgct cgactgactg tcaacgctga cgtaggatat tactcctgga ggtgtcccaa      60
gccctgaag  aaccgtgatg tcatcaccct ccgctcctgg ctcccatgg  gcgctgatta    120
catcattatg aactactcag tgaaacaccc taaataccca cctcggaaag acttggtccg    180
agctgtgtcc atccagacgg gctacctcat ccagagcacg gggcccaaga gctgtgtcat    240
cacctacctg gcccaagtgg accccaaagg ct                                    272
```

<210> SEQ ID NO 15
<211> LENGTH: 239
<212> TYPE: DNA
<213> ORGANISM: Rattus norvegicus
<220> FEATURE: -
<223> OTHER INFORMATION: 700137522H1
<221> NAME/KEY: unsure
<222> LOCATION: 194
<223> OTHER INFORMATION: a, t, c, g, or other

<400> SEQUENCE: 15

```
tcctggcccc caaggccatg aagaagatgt acaaggcctg catcaagtac cctgagtgga     60
agcagaaaca ccagccacat ttcaagccat ggctgcaccc ggagcagagc ccgttaccca   120
gcctggcgct gtcagagctg tcggtgcaac acgcagactc actggagaac atcgacgaga   180
gcgccgtgac aganagccgg gaggagcggg cgggtggagc aggagagggc agcgatgac    239
```

<210> SEQ ID NO 16
<211> LENGTH: 270
<212> TYPE: DNA
<213> ORGANISM: Rattus norvegicus
<220> FEATURE: -
<223> OTHER INFORMATION: 701435117T1
<221> NAME/KEY: unsure
<222> LOCATION: 2, 5, 34, 52, 74, 216
<223> OTHER INFORMATION: a, t, c, g, or other

<400> SEQUENCE: 16

```
anctnagcag gagcccagtg cccccaaaag gcangtgggg gaagggagga antgcagaag     60
gctcagtgcc ccanggttcc acnccagtcc tgtcttggtc cttgaagaga ggcggttctc   120
aggtgagtga tgtgtcgtca tcgctgccct ctcctgctcc acccgnccgc tcctcccggc   180
tctctgtcac ggcgctctcg tcgatgttct ccagtnagtc tgcgtgttgc accgacagct   240
ctgacagcgc caggctgggt aacgggctct                                      270
```

<210> SEQ ID NO 17
<211> LENGTH: 174
<212> TYPE: PRT
<213> ORGANISM: Mus musculus
<220> FEATURE: -
<223> OTHER INFORMATION: g897786

<400> SEQUENCE: 17

```
Ile Tyr Arg Leu Leu Asp Gln Pro Ser Gly Leu Tyr Glu Tyr Lys
  1               5                  10                 15

Val Phe Gly Val Leu Glu Gly Cys Ser Pro Ala Leu Leu Ala Asp
```

-continued

```
                    20                  25                  30
Val Tyr Met Asp Leu Asp Tyr Arg Lys Gln Trp Asp Gln Tyr Val
                35                  40                  45
Lys Glu Leu Tyr Glu Lys Glu Ser Asp Glu Gln Met Val Ala Tyr
                50                  55                  60
Trp Glu Val Lys Tyr Pro Phe Pro Leu Ser Asn Arg Asp Tyr Val
                65                  70                  75
Tyr Thr Arg Gln Arg Arg Asp Leu Asp Val Asp Arg Arg Lys Ile
                80                  85                  90
Tyr Val Val Leu Ala Gln Ser Ile Ser Ala Pro Gln Phe Pro Glu
                95                  100                 105
Lys Ser Gly Val Ile Arg Val Lys Gln Tyr Lys Gln Ser Leu Ala
                110                 115                 120
Ile Glu Ser Asp Gly Lys Lys Gly Ser Arg Val Phe Met Tyr Tyr
                125                 130                 135
Phe Asp Asn Pro Gly Gly Gln Ile Pro Ser Trp Leu Ile Asn Trp
                140                 145                 150
Ala Ala Lys Asn Gly Val Pro Asn Phe Leu Lys Asp Met Val Lys
                155                 160                 165
Ala Cys Gln Asn Tyr His Lys Lys Thr
                170
```